(12) United States Patent
Fei et al.

(10) Patent No.: US 7,194,914 B2
(45) Date of Patent: Mar. 27, 2007

(54) APPARATUS AND METHOD FOR SCANNING INTERNAL STRUCTURE OF O-RINGS

(75) Inventors: Dong Fei, Peoria, IL (US); Douglas A. Rebinsky, Peoria, IL (US)

(73) Assignee: Caterpillar Inc, Peoria, IL (US)

( * ) Notice: Subject to any disclaimer, the term of this patent is extended or adjusted under 35 U.S.C. 154(b) by 0 days.

(21) Appl. No.: 10/970,595

(22) Filed: Oct. 21, 2004

(65) Prior Publication Data
US 2006/0086192 A1   Apr. 27, 2006

(51) Int. Cl.
*G01N 29/04* (2006.01)
(52) U.S. Cl. ...................................................... 73/801
(58) Field of Classification Search ................. 73/801, 73/618, 620, 637; 356/73, 237, 387
See application file for complete search history.

(56) References Cited

U.S. PATENT DOCUMENTS

| | | | | |
|---|---|---|---|---|
| 3,813,543 A * | 5/1974 | Naya | ........................... | 356/393 |
| 4,062,633 A * | 12/1977 | Stapleton et al. | ........... | 356/638 |
| 4,143,553 A * | 3/1979 | Martens et al. | ............... | 73/625 |
| 4,177,679 A * | 12/1979 | Soldner | ........................ | 73/625 |
| 4,634,273 A * | 1/1987 | Farleman et al. | ............. | 356/73 |
| 4,650,334 A * | 3/1987 | Alster et al. | ................. | 356/612 |
| 4,808,001 A * | 2/1989 | Brenden et al. | ............ | 356/394 |
| 4,976,149 A * | 12/1990 | Ichikawa et al. | ............. | 73/597 |
| 5,952,578 A * | 9/1999 | White | ........................ | 73/622 |
| 6,065,345 A * | 5/2000 | Holenstein et al. | ........... | 73/660 |
| 6,626,834 B2 * | 9/2003 | Dunne et al. | ................ | 600/444 |
| 6,644,122 B2 * | 11/2003 | Borowczak et al. | .......... | 73/602 |
| 6,854,339 B2 * | 2/2005 | Moscaritolo et al. | ..... | 73/861.27 |
| 6,901,812 B2 * | 6/2005 | Moscaritolo et al. | ..... | 73/861.27 |
| 2004/0254466 A1 * | 12/2004 | Boner et al. | ................ | 600/447 |

* cited by examiner

*Primary Examiner*—Max Noori
(74) *Attorney, Agent, or Firm*—Liell & McNeil

(57) ABSTRACT

Some O-rings can include internal flaws that can eventually lead to failure of the O-rings during use. In order to scan an internal structure of an O-ring, the present disclosure includes an apparatus with an apparatus body to which an O-ring support and a transducer assembly are attached. The transducer assembly includes an ultrasound generator that transmits ultrasound toward the O-ring to generate reflections toward an ultrasound receiver. The apparatus includes a display for comparing ultrasound receiver data with expected data. It is determined whether there are reflections of the ultrasound transmissions off of at least one internal surface within the O-ring.

20 Claims, 3 Drawing Sheets

APPARATUS AND METHOD FOR SCANNING INTERNAL STRUCTURE OF O-RINGS

TECHNICAL FIELD

The present disclosure relates generally to O-rings, and more specifically to a non-destructive method and apparatus for scanning an internal structure of an O-ring.

BACKGROUND

O-rings are used in various applications in order to seal fluid volumes in mechanical parts against the movement of air and/or liquid. It has been found that O-rings can develop internal cracks, often referred to internal knit lines, during manufacturing. If an O-ring including an internal crack is not detected prior to the use of the O-ring, the crack may propagate to the O-ring surface, causing the O-ring to fail and allowing leakage. Depending on the application of the O-ring, the leakage can lead to failure of mechanical parts or undermine performance of a fluid handling device. For instance, certain fuel injectors, referred to as heavy fuel injectors, include passages through which coolant passes in order to cool the injectors. If a crack within an O-ring of the fuel injector propagates to the surface, the coolant can leak from the coolant passages within the fuel injector into fuel passages and eventually into a combustion chamber of an engine, causing engine performance problems.

In order to prevent problems caused by failing O-rings, O-rings used in critical applications are often inspected prior to use. Traditionally, O-rings have been visually inspected. Although defects on an outer surface of the O-ring can be visually detected, in order to determine whether there is an internal defect within the O-ring, the O-ring must often be cut open for inspection. Thus, in order to visual inspect an O-ring for internal cracks that can propagate during use of the O-ring, the O-ring must be destroyed. While such a strategy can be useful in statistically detecting O-rings with potential flaws out of a group of O-rings, defective O-rings will inevitably make their way into production fuel injectors. In addition, visual inspection is rather time-consuming because a lot of sectioning required to detect cracks over the entire perimeter of the O-ring.

The present disclosure is directed at overcoming one or more of the problems set forth above.

SUMMARY OF THE DISCLOSURE

According to one aspect of the present disclosure, an apparatus for scanning an internal structure of an O-ring includes an apparatus body to which an O-ring support and a transducer assembly are attached. The transducer assembly includes an ultrasound generator and an ultrasound receiver. The apparatus also includes a means for comparing ultrasound receiver data with expected data.

In another aspect of the present disclosure, in order to scan an internal structure of an O-ring, ultrasound is transmitted toward the O-ring. It is determined whether the transmitted ultrasound is reflected off of at least one internal surface within the O-ring.

DETAILED DESCRIPTION

Figure 1:
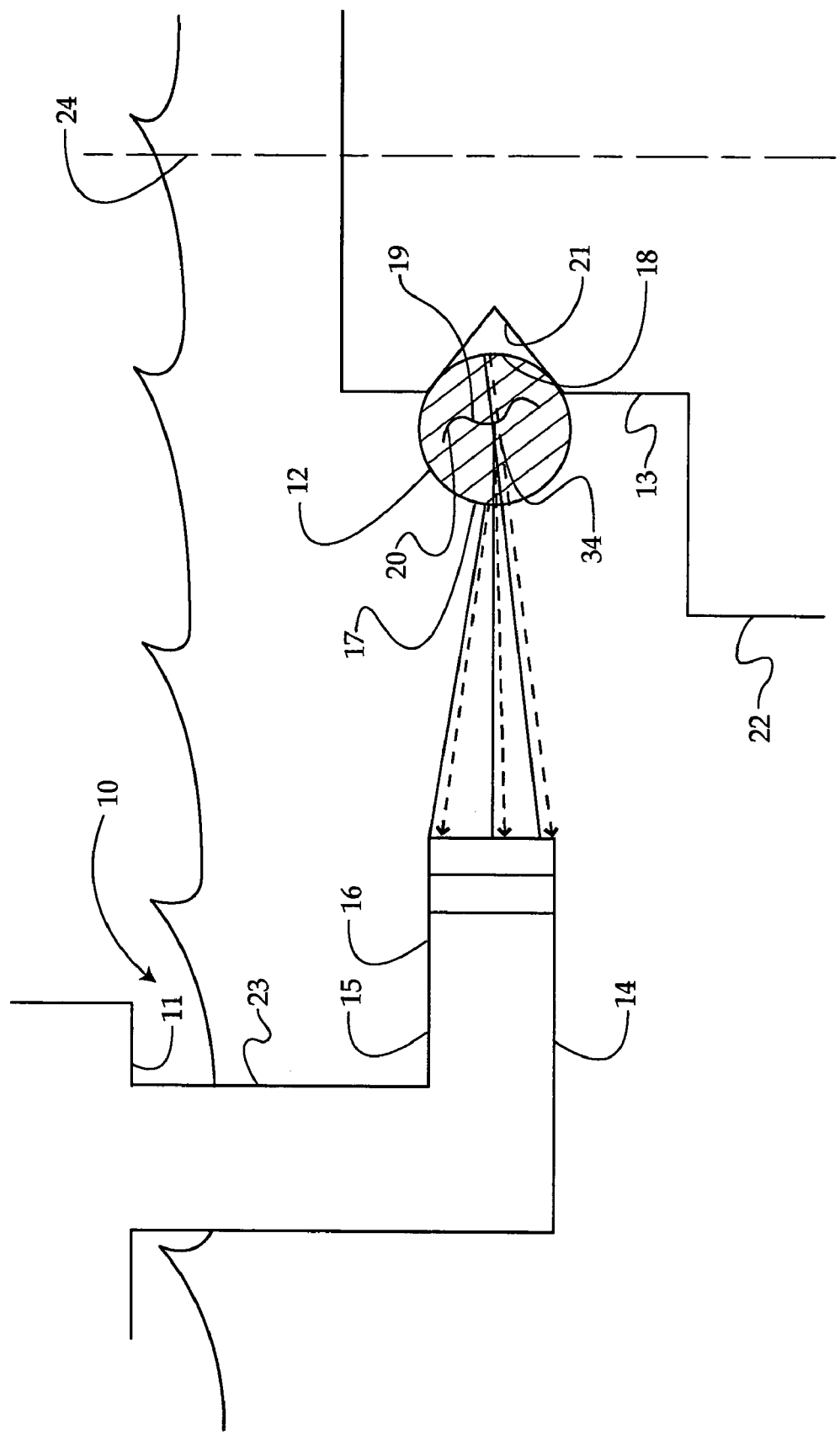
FIG. 1 is a cross-sectioned diagrammatic representation of an apparatus, according to the present disclosure.

Referring to FIG. 1, there is shown a cross-sectional diagrammatic representation of an apparatus 10 for scanning an O-ring 12. Although the illustrated O-ring 12 is an O-ring generally used in heavy fuel injectors and has a relatively small diameter, the present disclosure contemplates scanning any O-ring used to seal fluid volumes in mechanical parts regardless of the O-rings composition, of size, shape and application. For instance, the present disclosure contemplates O-rings with other cross sectional shapes, such as a D or square shape. Also, it need not have an overall O shape, but can be annular or even have separate ends, such as a segment, that acts as a seal in its particular application. It should be appreciated that the present disclosure also contemplates the apparatus 10 including various types of ultrasonic scanning systems, although the apparatus 10 preferably includes an ultrasonic immersion scanning system. The system could either be a commercially available ultrasonic immersion scanning system or a customized scanning system. The apparatus 10 includes an apparatus body 11 to which an O-ring support 13 and a transducer assembly 14 are attached. At least the transducer assembly 14 and the O-ring support 13 are immersed in a liquid, such as water, in order to better facilitate the propagation of ultrasound for scanning. The O-ring support 13 preferably can rotate with regard to the transducer assembly 14, although it should be appreciated that the transducer assembly 14 is moveable and could rotate about the O-ring support 13. The O-ring support 13 is attached to a turn-table 22 and defines an annular groove 21 in which the O-ring 12 can be secured. The O-ring 12 is manually loaded to and unloaded from the O-ring support 13. It should be appreciated that the present disclosure also contemplates automatic loading and unloading of the O-ring. The turn-table can preferably rotate 360° so that the O-ring 12 can be scanned at various angles without having to remove and remount the O-ring in order to get a complete scan. The apparatus 10 includes an adjustable scan step, being the degree of separation between ultrasound measurements. When scanning O-ring 12, the scan step is preferably set at approximately 0.3°. The smaller the scan step, the more likely that relatively small cracks will be detected, but the slower the process.

The transducer assembly 14 includes a search tube 23, an ultrasound generator 15, and an ultrasound receiver 16. Those skilled in the art will appreciate that the ultrasound generator 15 transmits ultrasound toward the O-ring 12. In the illustrated example, the ultrasound generator 15 transmits a focused, longitudinal wave ultrasonic pulse. Although the transducer assembly 14 has a center frequency of 10 MHz, it should be appreciated that the frequency of the ultrasound can vary. However, those skilled in the art will appreciate that the frequency is related to resolution. Thus, the frequency should be sufficiently high in order to provide the resolution required to detect relatively small internal surfaces defining defects having a size of concern for a particular application, but low enough that the ultrasound does not decay before penetrating into the O-ring 12 to a desired depth or completely therethrough.

The O-ring 12 includes an external surface, being a front surface 17 of the O-ring 12, and at least one internal surface, being a back surface 18 of the O-ring 12. O-ring 12 is defective and, thus, includes additional internal surfaces, being front and back surfaces 19 and 20 defining a defect, including a crack, void or inclusion within the internal structure. As illustrated, the transmitted ultrasound will reflect off of not only the front and back surfaces 17 and 18 of the O-ring 12, but also in general the front and back surfaces 19 and 20 of the defect. Preferably, for easiness of system alignment, as illustrated, a single ultrasonic transducer is used as both the ultrasound generator 15 and the ultrasound receiver 16 and is positioned within the assembly 14. Thus, in order for the ultrasound receiver 16 to receive ultrasound reflections off of surfaces 17 and 18 of the O-ring 12, the transducer assembly 14 is preferably orientated at an angle normal to the front and back surfaces 17 and 18 of the O-ring 12. Engineers have found that defects of concern within the internal structure of O-rings, such as O-ring 12, that are being used for fuel injectors are cracks generally parallel to a central axis 24 of the O-ring 12. Those skilled in the art will appreciate that ultrasound has maximum reflection when the ultrasound propagates normal to the orientation of the defect. Thus, preferably, the transducer assembly 14 is co-planar with the O-ring support 13 so that the ultrasound is reflecting off of the internal surfaces 19 and 20 of the crack at an angle normal to the surfaces 19 and 20. However, in order to detect defects with different orientations, the transducer assembly 14 can be moved so that the transducer may not be co-planar with the O-ring 12. For example, in order to detect if there are defects having surfaces generally perpendicularly to the central axis 24, the transducer assembly 14 can be orientated such that the assembly 14 transmits and receives ultrasound from the top of the O-ring 12. In addition, the present disclosure contemplates the ultrasound receiver 16 being separated from the ultrasound generator 15 and, thus, being positioned at an angle corresponding to the angle of orientation of the generator 15 and allowing the receiver 16 to receive ultrasound reflections from the O-ring 12 at different angles.

The ultrasound from the ultrasound generator 15 preferably includes a focal point 34 inside the O-ring 12. By focusing the ultrasound on the focal point 34 in the internal structure, the scanning system will be better able to detect small defects in the area around the focal point 34 at a given intensity. The resolution of the ultrasound will reduce with distance above and below the focal point 34. Thus, the focal point is preferably placed at the internal center point of the O-ring 12 so that defects above and below the focal point 34 can be both effectively defected. The scan step is set to be very small so that most of the internal structure is scanned. Moreover, it should also be appreciated that the smaller diameter O-ring being scanned, the more curved the front surface of the O-ring at which the ultrasound is contacting. By focusing the ultrasound on the inner center point, the ultrasound can contact curved upper and lower portions of the front and back surfaces 17 and 18 at an angle more normal to the surfaces 17 and 18. Thus, the ultrasound will reflect back to the ultrasound receiver 16 rather than scatter.

Figure 2A:
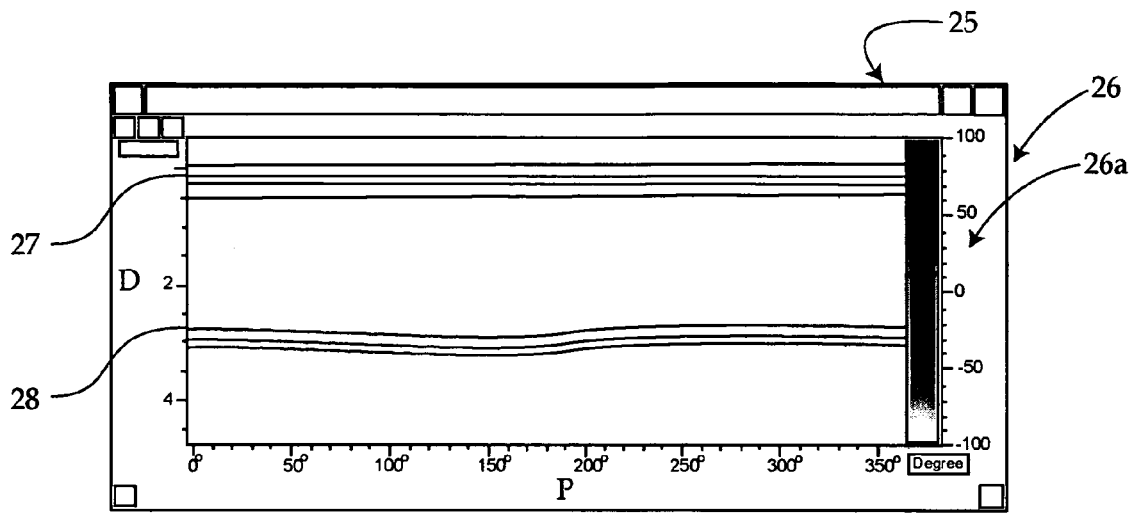
FIG. 2a is an ultrasound reflection image of an O-ring with no internal reflections, according to the present disclosure.
Figure 2B:
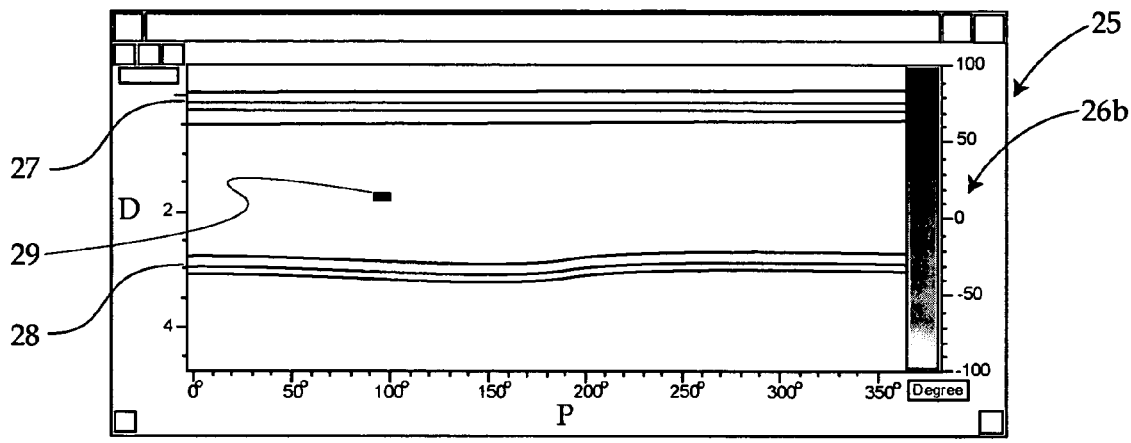
FIG. 2b is an ultrasound reflection image of the O-ring in FIG. 1 with a single internal crack.
Figure 2C:
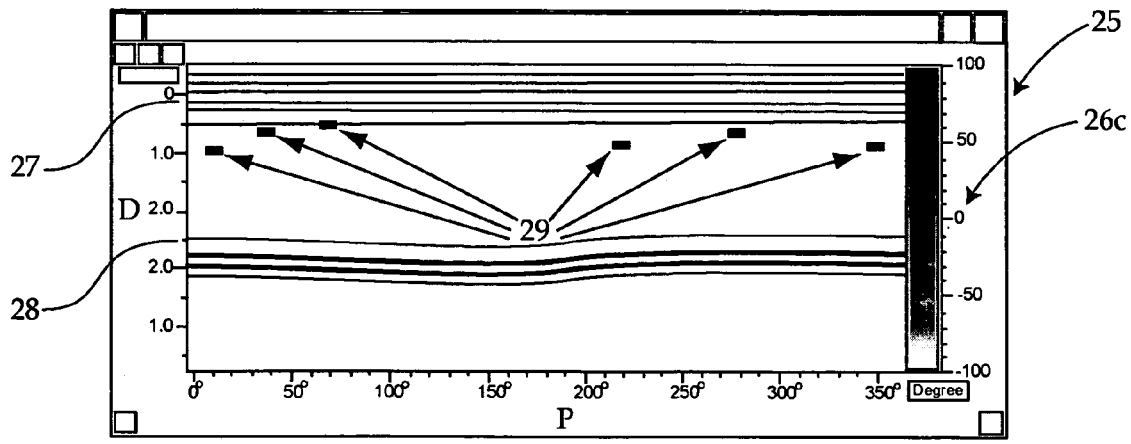
FIG. 2c is an ultrasound reflection image of an O-ring with multiple internal cracks, according to the present disclosure.

Referring to FIGS. 2a–c, there are shown ultrasound reflection images 26a, 26b, 26c of a defect-free O-ring, the O-ring 12, and an O-ring with multiple flaws, respectively. The apparatus 10 includes a display 25 for comparing ultrasound receiver data with expected data. In the illustrated example, the display 25 (shown in FIGS. 2a–c and 3a–b) is in communication with the ultrasound receiver 16 and is preferably operable to produce both an ultrasound reflection image 26 (shown in FIGS. 2a–c) and a time trace image 27 (shown in FIGS. 3a–b) of the type known in the art. A trained operator can determine whether there is an internal defect by comparing the ultrasound reflection image and time trace image with that of expected ultrasound reflection image and time trace image of a defect-free O-ring. However, the present disclosure also contemplates the means for comparing including a computer processor. For instance, the processor could compare the received ultrasound reflection data with a predetermined threshold amount of ultrasound reflection data from a defect-free O-ring at a known depth of the O-ring or ultrasound arrival time. If the received reflection data exceeded the predetermined reflection data, then the processor would determine and alert that the O-ring includes an internal flow with a particular orientation, and is thus defective. The present disclosure also contemplates other more advanced data processing techniques such as pattern recognition for automatic detection of defects in an ultrasound reflection image.

Referring still to FIGS. 2a–c, the angular position (P) at which the rotating O-ring is being scanned is illustrated on the horizontal-axis, and penetration depth (D) of the ultrasound is illustrated on the vertical-axis. Ultrasound reflection image 26b of O-ring 12 includes front and back constant bands 27 and 28 that represent ultrasound reflections off of the front surface 17 and the internal back surface 18 of the rotating O-ring 12, respectively. Similarly, both ultrasound reflection images 26a and 26c also include constant bands 27 and 28 at the depth representing the front and back surfaces of the O-rings. It is this aspect that can be used in calibrating so as to confirm penetration of the ultrasound completely through the O-ring. However, ultrasound reflection images 26b and 26c include internal individual bands 29 that occur only at a certain angle in the O-ring rather than throughout the 360° of the scan of the O-ring like bands 27 and 28. The individual bands 29 occur at various depths within the O-rings between the front and back surfaces. Thus, the individual bands 29 represent reflections off of the front and back surfaces of defects within the O-rings. For instance, in ultrasound reflection image 26b, the individual band 29 is caused by the reflection of ultrasound off of the front and back surfaces 19 and 20 of the flaw in O-ring 12.

Figure 3A:
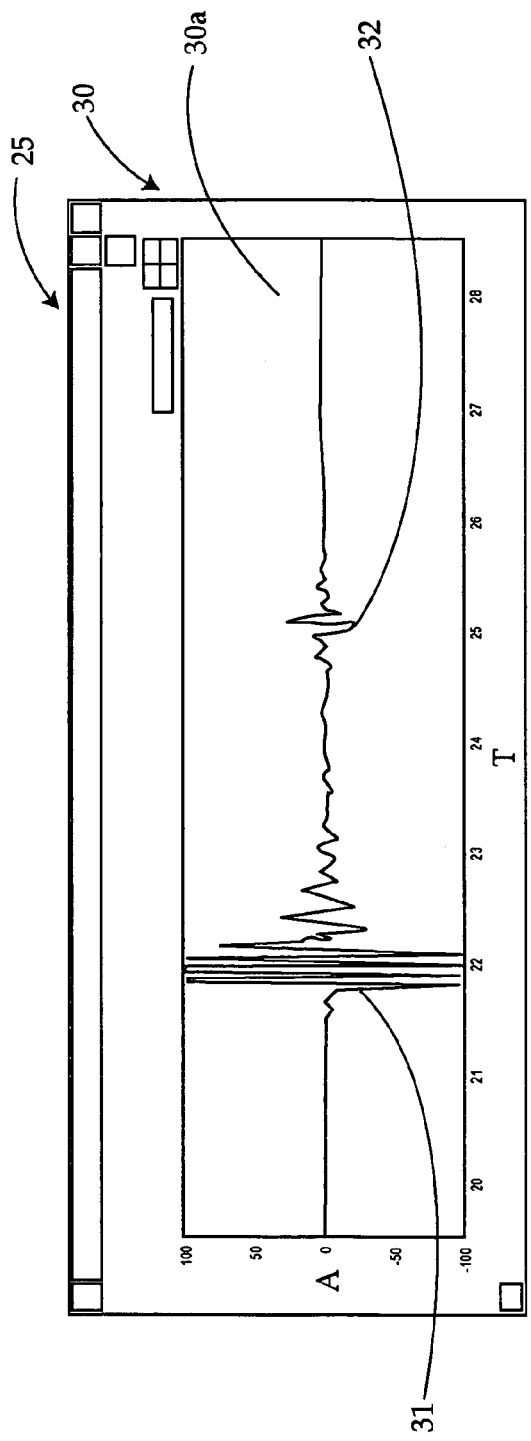
FIG. 3a is a time trace image of an apparently defect-free area of the O-ring in FIG. 1.
Figure 3B:
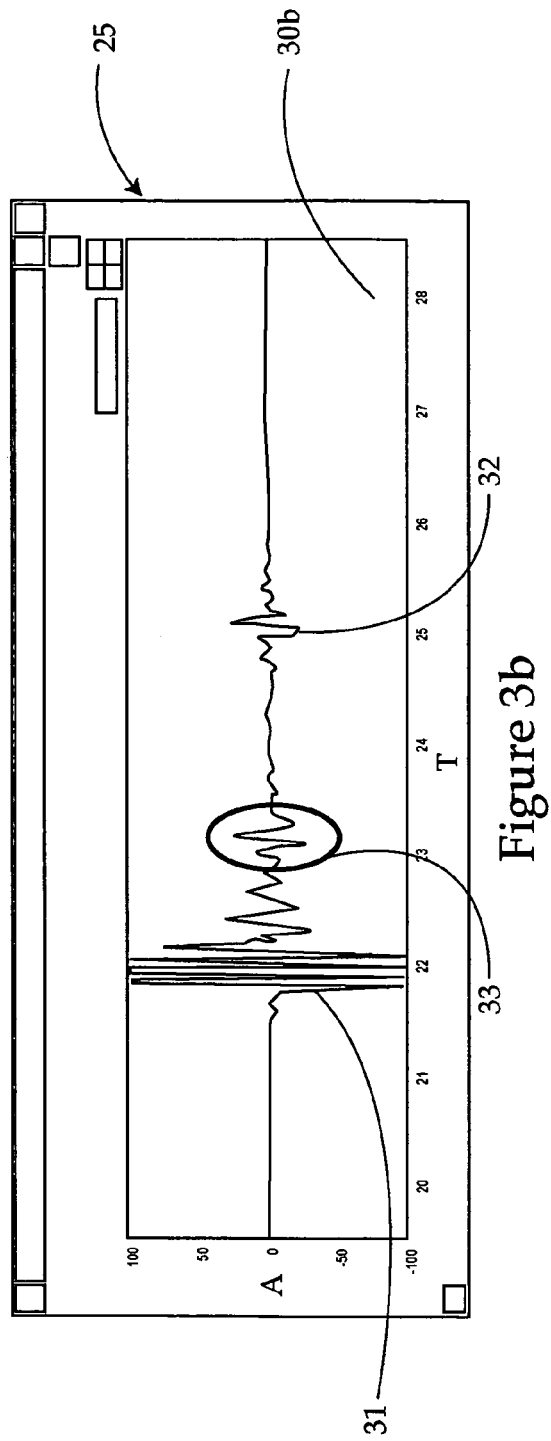
FIG. 3b is a time trace image of a defective area of an O-ring.

Referring to FIGS. 3a and 3b, there are shown time trace images 30a and 30b of a defect-free area and a defected area of O-ring 12, respectively. Ultrasound arrival time (T) is illustrated on the horizontal-axis, and amplitude (A) of the reflections is illustrated on the vertical-axis. Those skilled in the art will appreciate that the time trace images 30a and 30b are digitized outputs of the data from the ultrasound receiver 16. Whereas the time trace images 30a and 30b both include a first received reflection amplitude 31 indicating the front surface 17, and a second received reflection amplitude 32 indicating the back surface 18 of the O-ring 12, time trace image 30b includes a smaller additional received reflection amplitude 33 in between the first and second received reflections 31 and 32. Thus, the additional reflection amplitude 33 indicates ultrasound reflections off of the front and back surfaces 17 and 18 of the flaw within O-ring 12.

INDUSTRIAL APPLICABILITY

Referring to FIGS. 1–3b, a non-destructive method of scanning the internal structure of the O-ring 12 will be discussed. Although the present disclosure will be discussed for the O-ring 12 that is intended for use in a heavy fuel injector and has been found to include flaws oriented parallel or nearly parallel to the center axis 24 of the O-ring 12, it should be appreciated that the method can apply to detecting internal flaws within any O-ring regardless of the orientation of the flaws and the size and application of the O-ring.

In order to scan the internal structure of the O-ring 12, ultrasound is transmitted toward the O-ring 12. The transmitted ultrasound will reflect from the surfaces 17, 18, 19 and 20 of the O-ring 12. In the illustrated example, the O-ring 12 to be scanned is positioned within the annular groove 21 of the O-ring support 13, and the transducer assembly 14 is preferably orientated is at an angle normal to the front surface 17 of the O-ring 12. So that the ultrasound can reflect back to the ultrasound receiver 16 positioned within the transducer assembly 14. Further, the ultrasound is preferably focused at the focal point 34, being the internal center point, within the O-ring 12. Thus, the transmitted ultrasound generally contacts the curved portion of the front and back surfaces 17 and 18 of the O-ring 12 at an angle relatively normal to the curved surfaces 17 and 18. In addition, by focusing the ultrasound on the internal center point 34, the resolution of the ultrasound reflection image 26b is increased around the center point within the internal structure of the O-ring 12.

The ultrasound generator 15 and the ultrasound receiver 16 are orientated in order to detect the front and back surfaces 19 and 20 of the flaw that are in a predetermined orientation to the axis 24, which in the illustrated example, is generally parallel with the central axis 24. Engineers have found that the defects generally propagate vertically within the O-rings being manufactured to be used in heavy fuel injectors. However, internal defects having different orientations may also be of concern. Because in the illustrated example, the ultrasound generator 15 and ultrasound receiver 16 are positioned adjacent to one another or combined in a single device, the ultrasound is most sensitive to the internal surfaces 19 and 20 when contacting them at angle normal to the surfaces 19 and 20. Thus, the ultrasound generator 15 and the ultrasound receiver 16 both are co-planar with the O-ring 12 attached to the O-ring support 13 so that the ultrasound contacts the internal surfaces 19 and 20 at an angle normal to the internal surfaces 19 and 20. Those skilled in the art will appreciate that regardless of the orientation of internal surfaces to the central axis 24, the transducer assembly 14 is preferably oriented such that the ultrasound contacts the surfaces at an angle close enough to normal to the surfaces that the ultrasound penetrates rather than being scattered out of the plane of interest. For instance, in order to scan for defects that are perpendicular to the central axis 24, the transducer assembly 14 would be oriented above the O-ring 12 and transmit ultrasound from the top of the O-ring 12. It should also be appreciated that internal surfaces that are not at an angle normal to the ultrasound may still be illustrated on the ultrasound reflection image, but may not be as pronounced.

After transmitting ultrasound toward the O-ring 12, it is determined whether the ultrasound transmissions reflected off of at least one internal surface 18, 19 or 20 within the O-ring 12. The reflected ultrasound from the surfaces 17, 18, 19 and 20 of the O-ring 12 are received by the ultrasound receiver 16. The received ultrasound reflections are compared with the expected reflections. In the illustrated example, the received reflections from the ultrasound transmitted toward the O-ring 12 are displayed on the display 25 as the ultrasound reflection image 26b. From previous experience and experimentation, engineers have found that the expected reflection for a defect-free O-ring will be displayed as the ultrasound reflection image 26a with the front constant band 27 and the back constant band 28 caused by the reflections off of the front and back surfaces of the O-ring. The areas between the bands 27 and 28 are clear because there are no internal reflections caused by the discontinuity of internal flaws. By comparing the ultrasound reflection image 26b for O-ring 12 with the expected reflection image 26a, it can be determined that the ultrasound penetrated through the O-ring 12 and reflected off of the back surface 18 due to the constant band 28. However, because there is the additional band 29 that did not appear in the ultrasound reflection image 26a of the defect-free O-ring, the ultrasound also reflected off of additional internal surfaces, being the front and back surfaces 19 and 20 of the flaw. Thus, O-ring 12 is defective. Similarly, based on ultrasound reflection images shown in FIG. 26a with multiple individual bands 29 at depths between the front and back bands 27 and 28, one can determine that this O-ring includes multiple internal flaws.

The received reflections can also be compared with the expected reflections by displaying the received reflections as the time trace image 30. Whereas the time trace image 30a of a defect-free area of the O-ring 12 includes only the first and second received reflections 31 and 32, the time trace 30b for the defected area of O-ring 12 includes the additional received reflection 33 between the first and second received reflections 31 and 32. The additional received reflection amplitude 33 will generally be smaller than the first received amplitude 31 and will be generally larger than the second reflection amplitude 32. It can be determined that the additional amplitude 33 was caused by reflections off of the internal surfaces 19 and 20 other than the back surface 18 of the O-ring 12. It should be appreciated that the comparison between expected reflections and received reflection could be made by a processor, thus eliminating the need for a display of any type and operator subjectivity. Moreover, the apparatus could include both the display for the operator and the comparison by the computer for added assurance that defects are not being overlooked. Thus, if the comparison process were automated, no image would need to be generated.

When measuring the received reflections, there are multiple ultrasound transducer assembly variables that can be adjusted to obtain a predetermined ultrasound penetration depth and/or a predetermined resolution of the ultrasound reflection image 26b. The predetermined ultrasound penetration depth is preferably the width of the O-ring as it sits within the O-ring support 13. Thus, if the ultrasound reflection image does not include the back constant band 28, the predetermined ultrasound penetration depth has not been received. In order to increase the ultrasound penetration depth and scan the width of the O-ring 12, transducer assembly variables, such as an ultrasound frequency and/or ultrasound intensity, can be adjusted. In the illustrated example, the ultrasound frequency includes a center frequency of 10 MHz. By decreasing the frequency, there is less attenuation of the ultrasound wave within the O-ring 12, thus allowing greater penetration through the O-ring 12. One can also increase ultrasound intensity to bring up the ultrasound-reflection from the back surface 18. But this would also increase the width of the front band 27, making smaller the width of the O-ring that can be examined.

The predetermined resolution is a resolution in which relatively small defects within the O-ring 12 can be detected. The predetermined resolution can be initially established during calibration of the apparatus 10 by scanning an O-ring with a known defect. The ultrasound transducer assembly variables, such as ultrasound intensity and frequency, can be adjusted until the known defect is apparent from the ultrasound reflection image 26. When scanning the O-ring, if the ultrasound resolution image 26 is unclear, the resolution can be adjusted, at least in part, by increasing the ultrasound frequency and/or decreasing scan step size. Increasing the ultrasound frequency makes the focal spot in the O-ring 12 smaller and decreasing the scan step size allows more of the internal structure of the O-ring 12 to be scanned, both permitting small defects to be detected. However, those skilled in the art will also appreciate that the increased frequency may cause more attenuation of the ultrasound within the O-ring material, generally elastomeric, causing the depth penetration of ultrasound to decrease. Thus, the operator can adjust the intensity and frequency in order to obtain the predetermined resolution while penetrating to the back surface 18 of the O-ring 12.

Those skilled in the art will appreciate that there are transducer assembly variables other than ultrasound intensity, frequency, and scan step, including, but not limited to, scan speed, ultrasound wave mode, transducer orientation, and transducer focal length, that can be adjusted. For example, by increasing focal length, the ultrasound can scan a larger portion of the O-ring, but the resolution will be decreased. Further, in the illustrated example, the transducer assembly 14 is co-planar with the O-ring 12 to detect vertical defects. Even if the operator had little insight into the orientation of the flaws within the O-ring, the O-ring could be scanned multiple times with the orientation of the transducer assembly 14 to the central axis 24 of the O-ring changing with each scan. Thus, the transducer assembly variables can be adjusted such that the present disclosure can find use in any application, such as engines, aircraft and spacecraft, in which O-rings are used.

The present disclosure is advantageous because it provides a relatively quick, non-destructive method of detecting internal flaws, within O-rings. The present disclosure provides manufacturers with relative assurance that each O-ring being used in a critical application is free of internal defects that could lead to O-ring failure. By detecting defects prior to use, costly mechanical failures caused by leaking O-rings can be reduced. For example, by sorting the defective O-rings from the non-defective O-rings used in fuel injectors, the risks associated with O-ring failure in the engines in which the fuel injectors are being used are mitigated.

In addition to reducing the risk of and costs associated with the use of defective O-rings, the present disclosure can aid in monitoring the quality of O-ring production and developing improved O-rings. Often, O-ring defects, such as knit lines, occur during manufacturing. If defective O-rings are consistently being manufactured, the manufacturing process can be studied and altered to the stop the production of the defected O-rings. Further, by viewing internal structure of an O-ring without destroying the O-ring, researchers can study the effects that the manufacturing process and different applications have on the O-rings. Determining the causes of and structural precursors to O-ring failure can lead to higher quality O-rings and a reduction in O-ring failure.

It should be understood that the above description is intended for illustrative purposes only, and is not intended to limit the scope of the present disclosure in any way. Thus, those skilled in the art will appreciate that other aspects, objects, and advantages of the disclosure can be obtained from a study of the drawings, the disclosure and the appended claims.

What is claimed:

1. An apparatus for scanning an internal structure of an O-ring, comprising:
   an apparatus body;
   an O-ring support being supported by the apparatus body;
   a transducer assembly being supported by the and body and including an ultrasound generator and an ultrasound receiver; one of the transducer assembly and the O-ring support being rotatable with regard to the other; and
   an ultrasound reflection image display for comparing a number of reflections in ultrasound receiver data with a number of reflections in expected data.

2. The apparatus of claim 1 wherein the transducer assembly and the O-ring support being coplanar.

3. The apparatus of claim 1 wherein the display being in communication with the ultrasound receiver and being operable to produce an ultrasound reflection image that includes a front surface reflection, an internal crack reflection and a back surface reflection arranged in series.

4. The apparatus of claim 1 wherein the display being in communication with the ultrasound receiver and being operable to produce a time trace image.

5. The apparatus of claim 1 wherein the ultrasound from the ultrasound generator includes a focal point inside the internal structure of the O-ring.

6. The apparatus of claim 5 wherein the focal point being an internal center point within a material of the O-ring.

7. An apparatus of claim 6 wherein the transducer assembly and the O-ring support being rotatable with regard to the other, and the transducer assembly and the O-ring support being co-planar; and
   the display being in communication with the ultrasound receiver and being operable to produce an ultrasound reflection image and a time trace image.

8. A method of an internal structure of an O-ring comprising the step of:
   transmitting ultrasound toward the O-ring;
   detecting a front surface ultrasound reflection;
   detecting a back surface ultrasound reflection; and
   determining whether there are reflections of ultrasound transmissions off of at least one internal crack surface within the O-ring located between the front surface and the back surface.

9. The method of claim 8 wherein the step of transmitting includes a step of focusing the ultrasound at a focal point within a material of the O-ring.

10. The method of claim 8 wherein the step of transmitting ultrasound includes a step of orienting at least a portion of the ultrasound at an angle normal to an external surface of the O-ring.

11. The method of claim 8 wherein the step of determining includes a step of comparing a number of received reflections with an expected number of reflections.

12. The method of claim 11 wherein:
   the step of comparing includes a step of displaying the received reflections as an ultrasound reflection image that includes at least two reflections; and
   the step of determining includes determining that there is an ultrasound reflection off of at least one internal surface of the O-ring if the displayed ultrasound reflection image includes at least three reflections.

13. The method of claim 12 wherein the step of displaying includes a step of adjusting at least one of an ultrasound transducer assembly variable to obtain at least one of a predetermined ultrasound penetration depth and resolution of the ultrasound reflection image.

14. The method of claim 13 wherein the step of adjusting includes a step of increasing at least one of an ultrasound intensity and an ultrasound frequency in order to increase resolution of the ultrasound reflection image.

15. The method of claim 13 wherein the step of adjusting includes a step of decreasing an ultrasound frequency in order to increase the ultrasound penetration depth.

16. The method of claim 8 including a step of orienting an ultrasound generator and ultrasound receiver in order to detect the at least one internal crack surface being in a predetermined orientation with respect to a central axis of the O-ring.

17. The method of claim 16 wherein the predetermined orientation being generally parallel with the central axis of the O-ring.

18. The method of claim 12 wherein:
the step of comparing includes displaying the received reflections as an ultrasound reflection image that includes at least a front surface band and a back surface band via a display wherein each of the bands is disposed at a position corresponding to an ultrasound penetration depth of the O-ring; and
the step of determining includes determining that there is an ultrasound reflection off of at least one internal surface of the O-ring if the displayed ultrasound reflection image includes an internal surface band disposed between the front surface band and the back surface band.

19. The method of claim 12 wherein:
the step of comparing includes displaying the received reflections as an ultrasound reflection image that is a dime trace image including at least a front surface amplitude and a back surface amplitude; and
the step of determining includes determining that there is an ultrasound reflection off of at least one internal surface of the O-ring, if the displayed ultrasound reflection image includes an internal surface amplitude disposed between the front surface amplitude and the back surface amplitude.

20. A method of scanning an internal structure of an O-ring comprising the steps of:
transmitting ultrasound into the internal structure of the O-ring;
reflecting the ultrasound off of a plurality of O-ring surfaces;
determining whether there are reflections of ultrasound off of at least one internal crack surface of the O-ring, at least in part via a step of determining a relative penetration depth of each of a plurality of ultrasound reflections signals.

* * * * *

UNITED STATES PATENT AND TRADEMARK OFFICE
CERTIFICATE OF CORRECTION

| | | |
|---|---|---|
| PATENT NO. | : 7,194,914 B2 | Page 1 of 1 |
| APPLICATION NO. | : 10/970595 | |
| DATED | : March 27, 2007 | |
| INVENTOR(S) | : Dong Fei et al. | |

It is certified that error appears in the above-identified patent and that said Letters Patent is hereby corrected as shown below:

In Column 8, Claim 1, line 11, please replace the word "and" with the word --apparatus--.

In Column 10, Claim 19, line 9, please replace the word "dime" with --time--.

Signed and Sealed this

Nineteenth Day of June, 2007

JON W. DUDAS
*Director of the United States Patent and Trademark Office*